(12) United States Patent
Jansen

(10) Patent No.: US 9,744,027 B2
(45) Date of Patent: Aug. 29, 2017

(54) INTRAOCULAR LENS, IN PARTICULAR CILIARY INTRAOCULAR LENS

(71) Applicant: BIOLNIC UG, Köln (DE)

(72) Inventor: Josef Jansen, Bergisch-Gladbach (DE)

(73) Assignee: Biolnic UG, Cologne (DE)

( * ) Notice: Subject to any disclaimer, the term of this patent is extended or adjusted under 35 U.S.C. 154(b) by 0 days.

(21) Appl. No.: 14/423,028

(22) PCT Filed: Aug. 21, 2013

(86) PCT No.: PCT/DE2013/000471
§ 371 (c)(1),
(2) Date: Feb. 20, 2015

(87) PCT Pub. No.: WO2014/029382
PCT Pub. Date: Feb. 27, 2014

(65) Prior Publication Data
US 2015/0216652 A1 Aug. 6, 2015

(30) Foreign Application Priority Data
Aug. 24, 2012 (DE) .......................... 10 2012 016892

(51) Int. Cl.
*A61F 2/16* (2006.01)
(52) U.S. Cl.
CPC .............. *A61F 2/16* (2013.01); *A61F 2/1613* (2013.01); *A61F 2/1648* (2013.01);
(Continued)
(58) Field of Classification Search
CPC .... A61F 2/1635; A61F 2/1613; A61F 2/1648; A61F 2/1624; A61F 2/1629
See application file for complete search history.

(56) References Cited

U.S. PATENT DOCUMENTS 6,443,985 B1    9/2002  Woods
8,603,165 B2 *  12/2013 Park ...................... A61F 2/1635
                                                     623/6.23
(Continued)

OTHER PUBLICATIONS

International Search Report (in German with English Translation) for PCT/DE2013/000471, mailed Jul. 4, 2014; ISA/EP.

*Primary Examiner* — David H Willse
*Assistant Examiner* — Tiffany Shipmon
(74) *Attorney, Agent, or Firm* — Harness, Dickey & Pierce, P.L.C.

(57) ABSTRACT

The present invention relates to an intraocular lens, in particular a ciliary intraocular lens having at least one optic and one haptic element. In order to create an intraocular lens that enables a symmetrical deformation of one or several optic elements of the intraocular lens as well as a relative displacement of these optic elements on their optical axis to each other, so that a sufficient change in refractive power is achieved, it is proposed that the haptic element is composed of several haptic elements, preferably connected to the optic element in equiangular manner, wherein
a) the haptic elements have an essentially trapezoidal portion in a plan view and the bases of two adjacent haptic elements are connected to each other at the transition to the optic element and
b) the haptic elements on the side of the trapezoidal portions facing away from the optic element have a part of annular haptic ring segment, wherein the haptic ring segments of two adjacent haptic elements in the unloaded state are spaced slightly away from one another,
Furthermore, a method for implantation of an intraocular lens having at least one optic element and one haptic element, and a filling is claimed. According to the invention, the intraocular lens is folded or rolled to reduce the volume so that the filling is at least partially disposed in one or
(Continued)

Figure 2C:
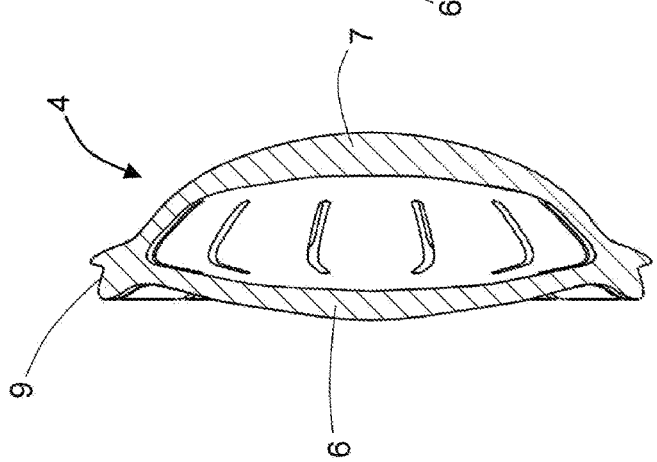

possibly several reservoir/s and the filling is at least partially pressed from the reservoir into the cavity after implantation.

20 Claims, 11 Drawing Sheets

(52) U.S. Cl.
CPC ....... *A61F 2/1629* (2013.01); *A61F 2002/169* (2015.04); *A61F 2002/1681* (2013.01); *A61F 2230/0006* (2013.01); *A61F 2230/0026* (2013.01); *A61F 2250/0003* (2013.01)

(56) References Cited

U.S. PATENT DOCUMENTS

| | | | |
|---|---|---|---|
| 2003/0149480 A1* | 8/2003 | Shadduck | A61F 2/1648 623/6.41 |
| 2004/0082993 A1* | 4/2004 | Woods | A61F 2/1613 623/6.28 |
| 2008/0161913 A1 | 7/2008 | Brady et al. | |

* cited by examiner

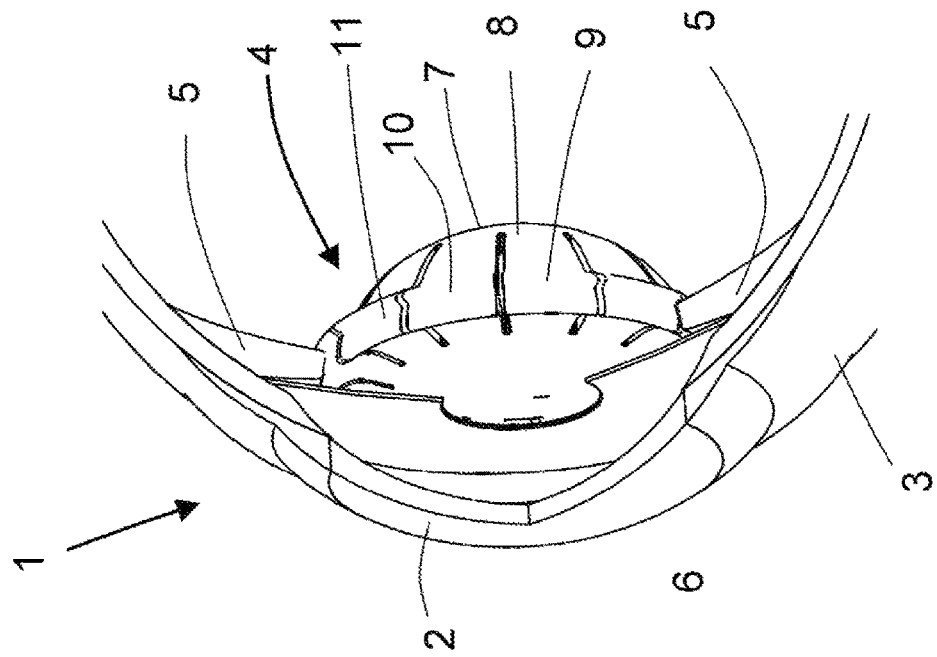
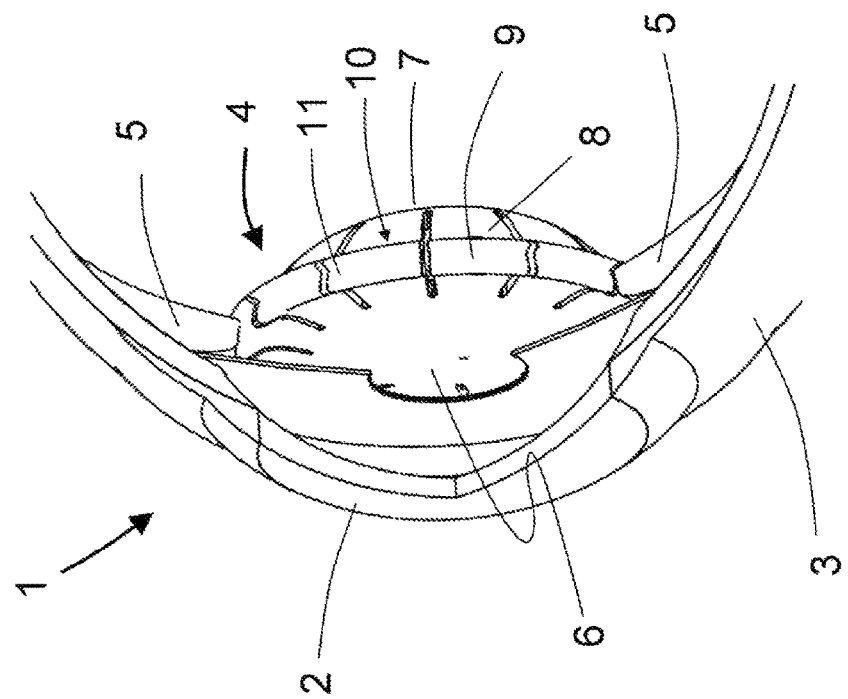

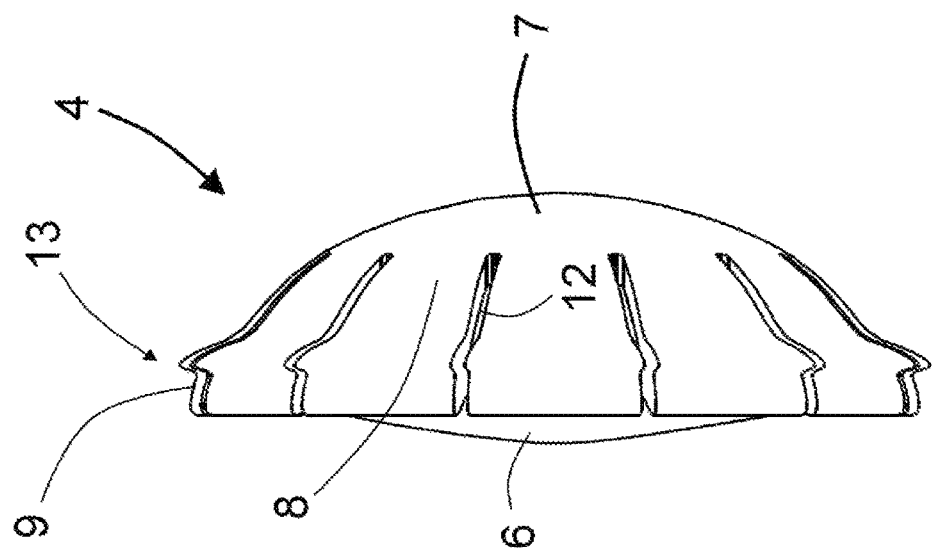
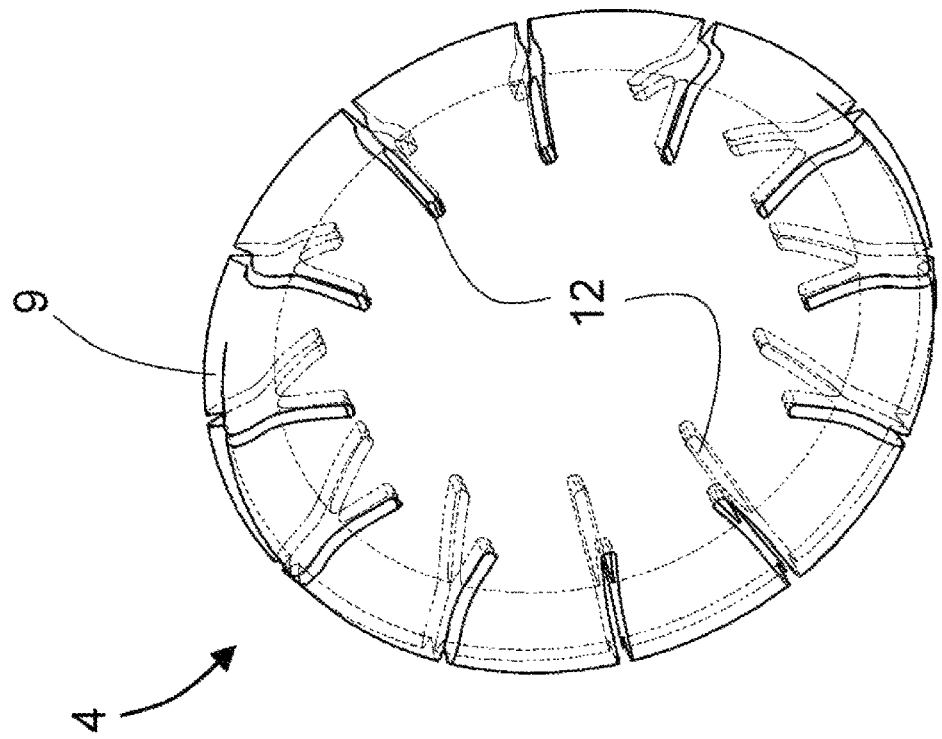
Fig. 2b
Fig. 2a

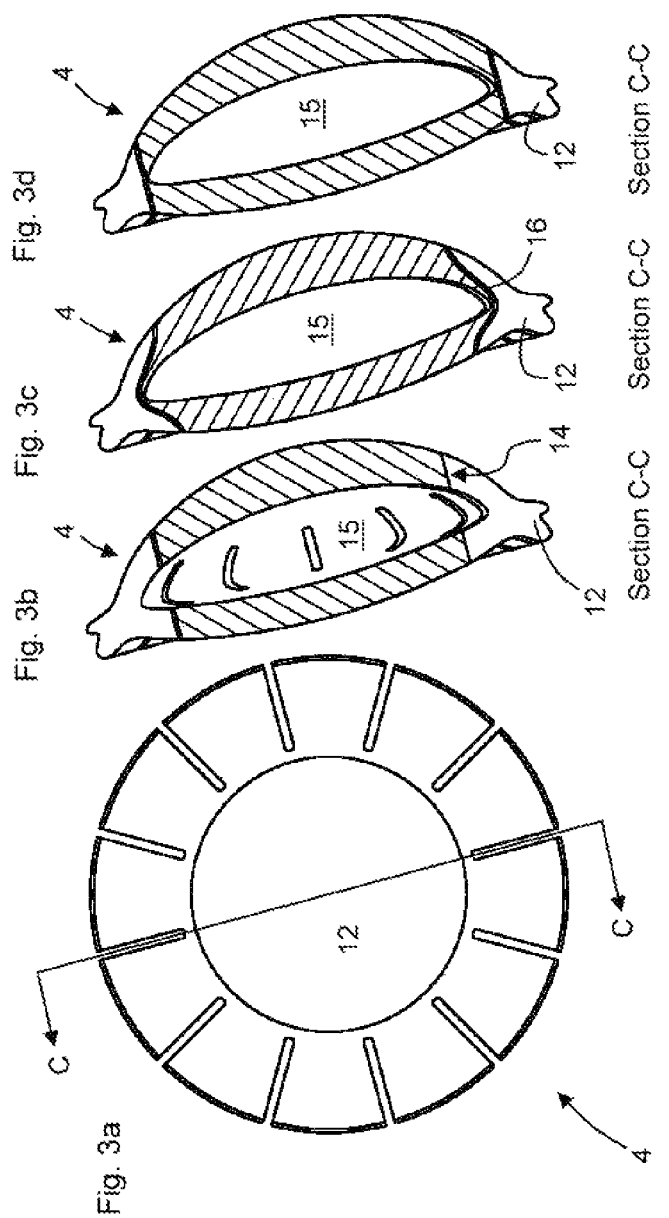

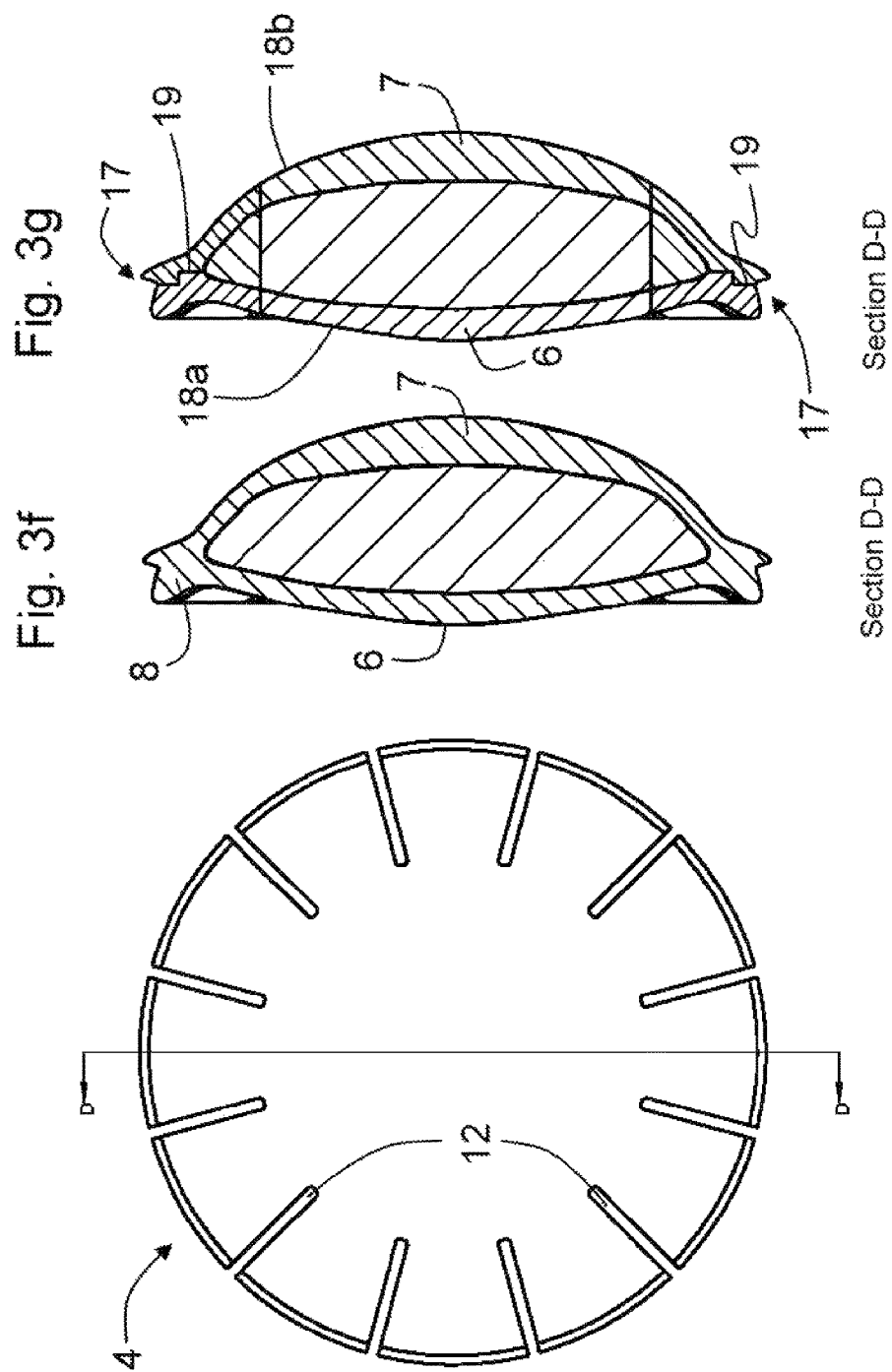

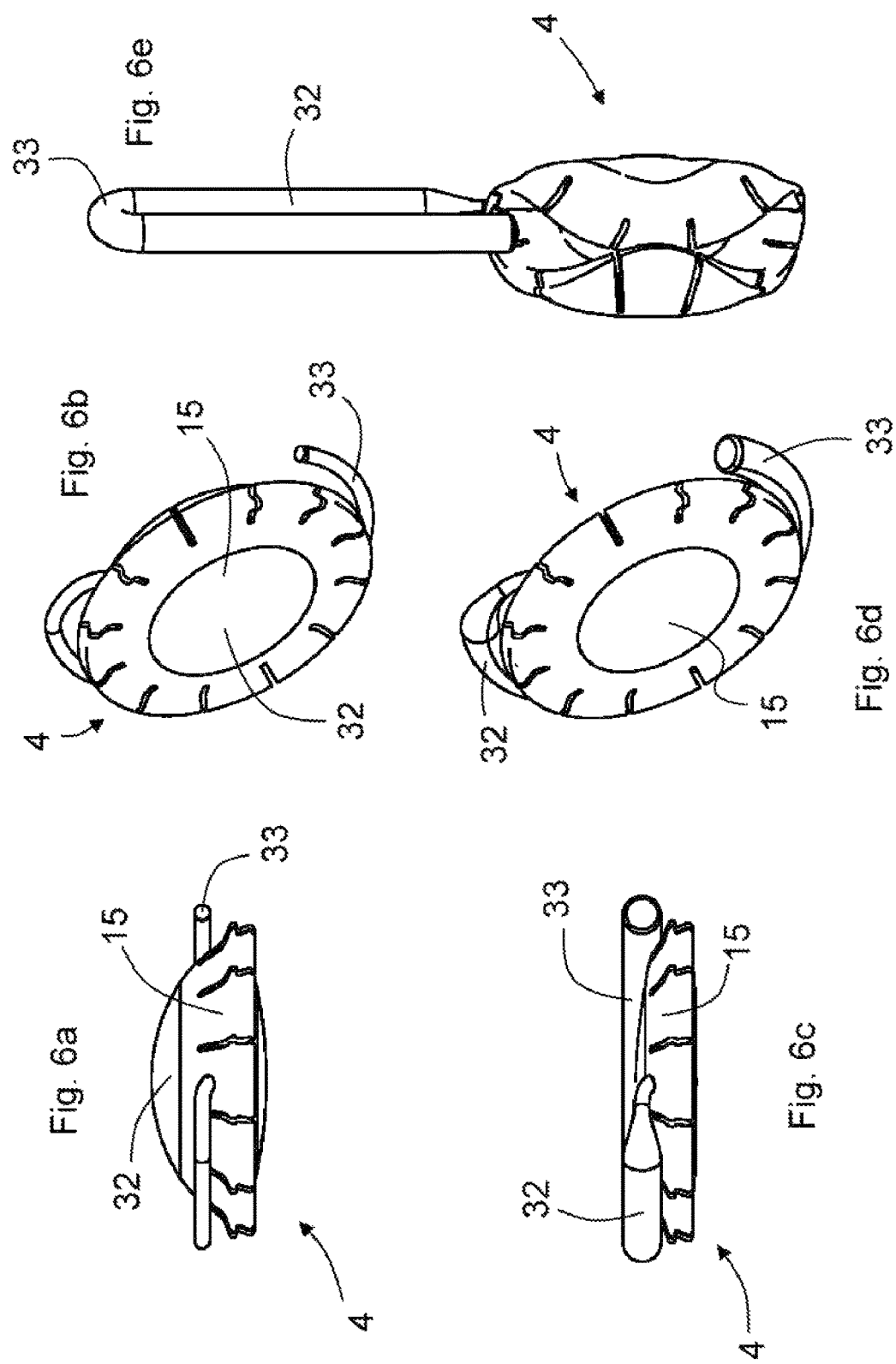

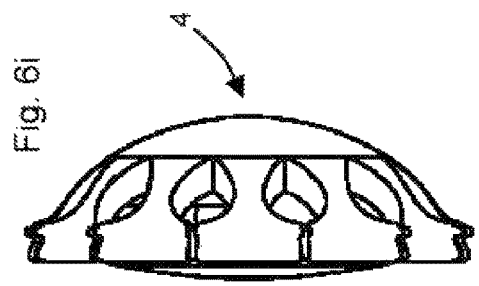
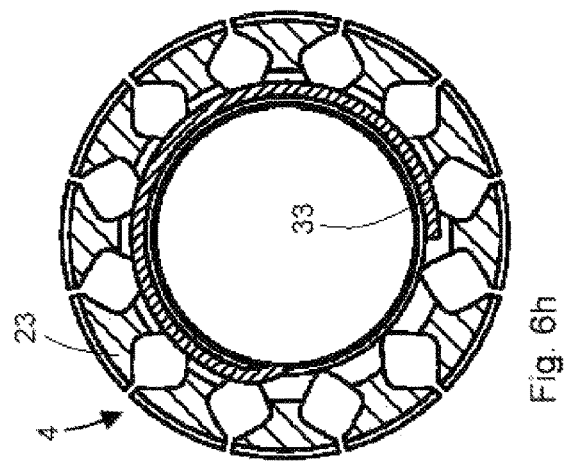
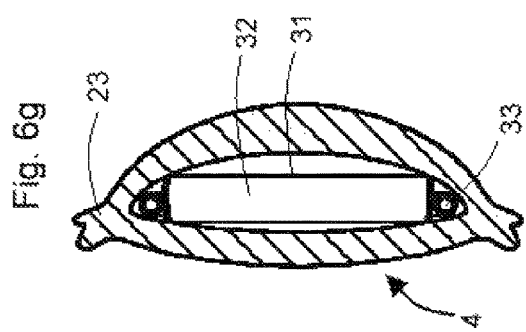
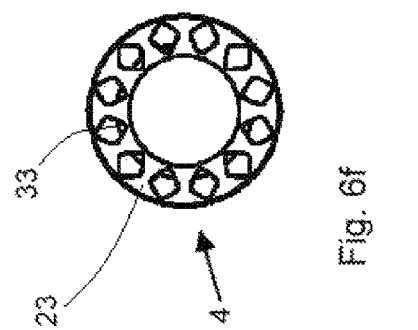

INTRAOCULAR LENS, IN PARTICULAR CILIARY INTRAOCULAR LENS

CROSS REFERENCE TO RELATED APPLICATIONS

This application is a U.S. National Phase Application under 35 U.S.C. 371 of International Application No. PCT/DE2013/000471 filed on Aug. 21, 2013 and published in German as WO 2014/029382 A1 on Feb. 27, 2014. This application is based on and claims the benefit of priority from German Patent Application No. 10 2012 016 892.6 filed Aug. 24, 2012. The entire disclosures of all of the above applications are incorporated herein by reference.

The present invention relates to an intraocular lens, in particular a ciliary intraocular lens having at least one optic and one haptic element. Furthermore, the invention relates to a method for implantation of an intraocular lens having at least one optic, one haptic element and a filling. Finally, the invention relates to an intraocular lens having at least one optic, one haptic element and at least one filling located in the optical area.

The so-called accommodation is the dynamic adaptation of the refractive power of the eye. In the near vision, the natural lens is in its spherical, non-deformed, and unloaded state in which no forces act on them. The ciliary muscle is thereby strained and concentrically contracted and the zonular fibres are relaxed. If the ciliary relaxes (far accommodation), the zonular and the capsular bag through its equator tighten in the radial direction. The capsular bag thereby exerts an axial compressive force on the lens, whereby the latter deforms into a less curved ellipse, so that the farsightedness is enabled. Upon contraction of the ciliary (near accommodation), the lens goes back by its own resilience in its own spherical form, which again is accompanied with an increase in refractive power. The diameter of ciliary and lens as well as the lens thickness vary between near and far vision by about 0.5 mm. The elasticity of the lens deteriorates as one gets older and eventually leads to presbyopia. The correction is usually done with a pair of glasses.

A particularly serious occurrence as age slowly progresses is cataract, which is opacification of eye lens. The consequences of such a cataract are increased glare sensitivity of the eye and the faded colour perception. Advanced cataract can only be treated surgically. For this purpose, the lens is first destroyed by ultrasound, vacuum-extraction, and then an artificial, usually rolled; intraocular lens is injected through a small incision in the cornea into the open capsular bag.

The known state of the art intraocular lenses are monofocal, thus they have only one focal point. Using the so-called haptic element elements, the optic elements of intraocular lenses are usually centred in the capsular bag. Aspherical lenses improve contrast and night vision by avoiding scattered light, while intraocular lenses with special (UV) filters protect the retina. Materials with a high refractive index are also advantageous to be able to produce thinner lenses or intraocular lenses for smaller incisions with the same dioptric power. Minor cuts must not be closed with a seam. In addition, the likelihood of postoperative astigmatism is significantly reduced.

In addition, according to the state of the art bifocal or multifocal lenses are known. The disadvantage of multifocal lies in the much poorer sensitivity to both contrast and increased glare.

The most common complication with the use of intraocular lenses is the postoperative after-cataract. This arises in large part by proliferation of residual or regenerated lens epithelial cells, remaining in the capsular bag after extracapsular cataract extraction. The after-cataract requires a laser treatment that can be associated with potential complications. A crease-free relaxation of the posterior capsular is considered as a possible effective after-cataract prophylaxis.

Despite numerous attempts, it has not yet been managed to restore accommodation of the eye with sufficient refractive power change for a longer period.

Most concepts for restoration of accommodation provide the implantation of an intraocular lens in the capsular bag ("capsular intraocular lenses").

Here, two basic approaches can be distinguished, namely intraocular lenses according to the so-called "optic element shift principle" and the lens capsular refilling ("lens refilling") with liquid or viscous materials. However, the lens capsular refilling has not been successful due to various problems.

In the optic element-shift principle, one or two optic elements are displaced along the optic elemental axis of the intraocular lenses. However, a sole displacement of the optic element on the optic elemental axis does not reach a satisfactory accommodative power, since the displacement is limited.

In addition, intraocular lenses that are not implanted in the capsular bag and with haptic element elements in direct contact with the ciliary (so-called ciliary intraocular lenses) also belong to the state of the art. For implantation, the capsular bag is initially removed or is at least located partially posterior of the intraocular lens after implantation. Such intraocular lenses can be used in the sulcus of the posterior chamber or the ciliary muscle or be attached to the sclera.

The main advantage of a ciliary intraocular lens compared with a capsular intraocular lens is in a significantly higher power transmission potential, caused by the direct connection to the ciliary, which can lead to a significantly higher accommodative power of the intraocular lens.

For example, such ciliary intraocular lens is disclosed in U.S. Pat. No. 4,892,543, whose 2 Ushaped haptic element arms are in connection only to a very limited extent with the ciliary and therefore allow only a limited radial loading capacity.

Another example is described in DE 10346024A1, where a spacer ring holds and centres the intraocular lens, which is formed into the sulcus and on the ciliary muscle. This design allows only one shift and no change in shape of the optic elements.

In US 2009/0012609A1 an embodiment of a ciliary intraocular lens is described in which both the thickness and the curvature of the optic element vary. However, sufficient radial force transmission is not possible for the same reasons described earlier.

The object of the present invention is to provide an intraocular lens that allows a symmetrical deformation of one or more optic elements of the intraocular lens as well as a relative displacement of these optic elements relative to each other on their optic elemental axis, so that a sufficient change in refractive power is obtained.

This object is met by the intraocular lens according to claim 1, in which, according to the invention, it is provided that the haptic element is composed of several haptic elements, which are preferably connected equiangular with the optic elements, wherein a) the haptic elements have an essentially trapezoidal portion in a plan view and the bases of two adjacent haptic elements are connected to each other at the transition to the optic element and b) the haptic elements on the side of the trapezoidal portions facing away from the optic element have a part of annular haptic ring segment, wherein the haptic ring segments of two adjacent haptic elements in the unloaded state are spaced slightly away from one another, so that an essentially cake-piece or line-shaped recess is formed between two adjacent haptic elements.

Due to the design according to the invention it is achieved that both the ciliary in the tensioned and the relaxed state has a maximum contact surface to the haptic ring segments, and that the haptic element has a maximum contact surface to the optic elements, whereby both over the circumference of haptic ring segments as well as over the circumference of the optic elements a uniform force distribution is created during accommodation. In this way, the optic element is uniformly deformed and/or moved evenly, thus avoiding errors.

Advantageous embodiments of the present invention are described below and in the subordinate claims.

According to a first preferred embodiment of the invention it is provided that the intraocular lens at least has an anterior and a posterior optic element, which are connected to each other via the haptic element, wherein a cavity is formed by the anterior and posterior optic elements as well as the haptic element and at least the optic area of the a cavity has a filling. Alternatively, it is provided also that the area of the cavity, which is bounded by the haptic element and/or the openings be partially occupied or completely by the filling. During accommodation, at least one of the lenses changes shape. The natural shape or production condition is preferably a flat shape for far vision.

The filling is in liquid, gel, or gaseous form according to a preferred embodiment of the invention and comprises nano-particles according to a particularly preferred embodiment. The filling serves to increase the accommodative power, for which the filling of the intraocular lens preferably has a higher refractive index than that of aqueous humour. In addition, the medium or material of the filling is softer and/or more elastic than the shell. The filling lies preferably fully against the two outer optic elements. The inner surfaces of the optic elements in this case may be of any shape, particularly when lenses and filling and where applicable the bag has the same refractive index. The filling can completely fill the interior of the intraocular lens, or be limited to the area of the optic element. If the filling extends beyond the optic elemental area in the haptic element and if the latter is not liquid or gaseous, then the filling in the section of the haptic element as the haptic element itself is preferably provided with openings, in particular when the filling is connected with the haptic element. The design of gel-like soft filling and harder shell, given appropriate thickness distribution of the shell and suitable modulus of elasticity, allows the controlled deformation of the intraocular lenses to achieve adequate optic elemental imaging in the near and far state, up to the border area of optic elements. Stray light problems can thus be prevented or reduced significantly even when the iris is wide open. Such a change in shape of the intraocular lens cannot be achieved if the filling would be surrounded by only a very thin or pliable membrane or shell.

The filling can be isolated within the intraocular lens. If the filling medium is liquid, it makes sense to integrate the filling inside a bag consisting of a very thin membrane. Alternatively, the filling can be separated from the rest of the intraocular lens and/or of the aqueous chamber radially outwardly by a membrane. The membrane spans in this case preferably between the respective bases of the anterior to the posterior haptic element, that is, between the edges of the lenses. The membrane may extend radially outwardly to compensate for a change in volume between far and near vision. Another possibility for sealing the cavity is to close the haptic element openings with a thin membrane. The membrane or bag that closes the cavity radially outwards is substantially thinner in comparison with the shell of an intraocular lens should lie in the order of about one-tenth of the thickness of the shell. The thickness of such a membrane is preferably between 5 µm and 50 µm.

The filling or the bag with the filling is preferably connected completely or also only partly with one or simultaneously with two optic elemental surfaces or it may lie loosely in the interior of the intraocular lens. Thus, also interstices can occur between external optic elements and the filling that fill with aqueous humour as the case may be. In addition, the filling may also be divided so that a gap or interstice is formed in the centre in each case and the divided fillings are connected to the external optic elements. The bag can be inserted through the openings into the interior of the intraocular lens.

According to an alternative embodiment, the filling consists of a hydrophilic material (hydro gel) such that the intraocular lens in the dry state and with a smaller volume can be easily implanted. After the implantation into the eye, the filling absorbs water from the aqueous humour and acquires the size and shape of the intended optic elemental function of the intraocular lens. For this design, the possibly existing, previously described, separating membrane or the intraocular lens itself should be waterpermeable. For this purpose, the membrane could be perforated, for example. Alternatively or additionally, only the haptic element could be perforated or permeable to water by diffusion, so that the aqueous humour can penetrate into the cavity.

With a liquid or gel-like filling, the intraocular lens can be implanted in a smaller state when the cavity is filled only after the implantation. It is therefore provided according to a preferred embodiment of the invention, that one or more reservoirs filled with the filling are preferably detachably connected via a tube to the cavity, so that, for a change in volume of the cavity during accommodation or folding of the intraocular lens for implantation the filling can be transferred into the reservoir and vice versa.

According to a preferred embodiment, the reservoir is tube-shaped and is preferably connected with the cavity via a micro-valve or via a cannula or hollow needle. Here, the tubular reservoir could be turned inside out over the end of the valve as a water tube via a shut-off valve. Alternatively, the reservoir can also be connected via a tube with the hollow space that can be separated by fusion. On the other hand, the tubular reservoir could be connected with the cavity by means of a cannula, which forms the open end of the reservoir. After removal of the cannula, the punctured spot closes again. In addition, the punctured spot in the form of a rubber plug or nipple ("rubber closure to be pierced") could be reinforced. Advantageous for tight sealing of the puncture is that the very soft polymers needed for such an intraocular lens are usually very sticky. Furthermore, the valve between the cannula and reservoir could be optionally connected. The connection or interface between the cavity and the reservoir is preferably disposed on the membrane, or on the haptic element or outside the optic element zone of the optic element. If necessary, the cavity is additionally connected to a vent tube in order to avoid any blistering effect. The vent tube can be analogously connected to the reservoir with the cavity. The advantages of the detachable reservoir for filling the cavity are that a pre-filled and pre-assembled intraocular lens with a defined capacity can be delivered to the ophthalmologist. In overall, incorrect manual processes such as incorrect filling quantities and/or contamination are reduced.

In other words, the filling of the cavity with the filling can be carried out by means of one or a plurality of (micro) supply tubes and a possibly necessary ventilation tube, which are connected to the cavity and sealed after filling of the cavity with the liquid, by micro-valves or terminals or grease nipple or be separated for example by welding.

The cavity could also be filled via a micro-metering pump. These operations can occur outside of the eye. The remaining tube rest after sealing the tube, which are connected to the cavity of the intraocular lens, can be moved into the interior of the eye and possibly pulled into the remaining cavity between haptic elements and membrane. The filling may also be injected via syringe. The filling process could be so used to adjust the refractive dioptre number.

Another possibility to implant the intraocular lens with the smallest possible volume into the eye is the introduction of the bag or the filling after the implantation via the haptic openings into the interior of the intraocular lens.

In a further embodiment of the invention, a tubular structure is coupled to the intraocular lens, which can be used in particular for the implantation process as a reservoir for filling the intraocular lens. For this purpose, a specially shaped tube is connected with one end to the cavity and/or filling and closed at the other end. With this, the liquid of the intraocular lens is coupled internally (with fluid) hydraulically to the reservoir. Preferably, the reservoir is guided anterior along the haptic ring or posterior in a particularly preferred manner. For implantation, the intraocular lens, for example, is initially compressed so that the medium is pumped from the interior of the intraocular lens into the tube while the tube is inflated, and then rolled up. After injection and development of the intraocular lens, the medium flows back into the cavity of the intraocular lens. A valve in the supply tube or other closure of the tube could thereby prevent unwanted and/or excessive back-flow from the interior into the tube. In addition, the tube can be used in its function as a reservoir in "normal operation" by compensating changes in volume of the filling of the intraocular lens during accommodation. The closed end of the tube may also take the form of a bubble.

In an alternative embodiment, the reservoir is connected internally to the membrane or bag. The tube can be particularly routed outwards via one of the haptic openings so that it can swell during implantation of the intraocular lens. After implantation, the tube can remain in the eye chamber, or it may be drawn particularly in the case of use as a capsular intraocular lens into the interior of the intraocular lens and be placed in the circumferential direction around the filling. The tube and/or the reservoir then lie between the haptic element and the final filling membrane or bag.

The described embodiments are also provided in intraocular lenses that have multiple reservoirs, which may be possibly also designed differently from each other.

The tubes have a diameter preferably between 0.1 mm and 1 mm, particularly preferably between 0.3 mm and 0.8 mm, and a length of about 35 mm. The section of the tube that is to be formed as a reservoir, if necessary, can also accept larger diameters, e.g. have a bubble form and thinner wall than the rest of the tube. As stated above, a plurality of tubes can be distributed over the intraocular lens and be connected with the interior.

The intraocular lens preferably consists of two essentially (from anterior to posterior) convex-concave or concave-convex-shaped, half-shells with optic elements integrated at the poles, which are connected with each other at their equator and/or via their haptic element. Dual curved shells can be deformed into less curved or flat shells only with relatively large forces. Therefore, the haptic element part of the intraocular lens from the equator to the lens has radially aligned recesses, whereby the deformation forces of the shells needed for a change in refractive power are significantly reduced. The recesses open according to a preferred embodiment, the inner and/or cavity of the intraocular lens, so that openings are formed, which open the cavity radially outwards. Without loss of contractility, it is provided according to a preferred embodiment that the openings be closed by a membrane or skin.

Preferably, the recesses are routed starting radially within the haptic element from the equator, and
  a) terminate within the haptic element,
  b) lead to the equator of the optic element or
  c) beyond the equator of the optic element.

In the variants a) and b) the cavity can be designed open or closed depending on the design of the haptic element. In variant c), the cavity is opened, wherein the recesses can also be introduced up to a thin membrane, whereby the cavity also remains closed.

In order to allow possibly uniform force distribution along the circumference of the optic element, the ciliary under load lies completely on the haptic ring segments. In the unloaded state, therefore, a minimum gap or a minimum recess arises between the haptic ring segments, so that the ciliary in the unloaded state does not lie fully on the haptic ring segments. In the case of line-shaped recesses, trapezoidal or line-shaped haptic elements form. According to a preferred embodiment, the cumulative width of the recesses on the outer diameter of the haptic ring in the unloaded state is less than 40%, preferably less than 25% and more preferably less than 2-15% of the circumference. In order to avoid slipping of the optical system or of the intraocular lens within the ciliary, the haptic ring segment form a cylindrical outer contour, and are preferably V-shaped in configuration in cross-section, so that these conform to the contour of the ciliary possibly form-fitting and/or also allow insertion as far as possible into the sulcus. The haptic can also only be supported on the ciliary where, possibly, additional arm or check mark is attached to the ciliary in the sulcus and/or haptic element. To allow more efficient power transmission, it is provided that the area standing in contact with the ciliary is covered with a thin and soft, fine fibrillar or with a porous structure so that surrounding cells can grow there and lead to a strong bond between ciliary and haptic element. Alternatively, it is provided that the area of the haptic element in contact with the ciliary itself is micro-porous. In addition, it is envisaged that this fine fibrillar or porous structure of the intraocular lens is sewn or attached to the surrounding tissue by means of threads or self-closing clips. Such a positive connection, however, is also proposed without the fine fibrillar or porous structure on the haptic element.

Analogous to the design of the haptic ring segment, the bases of the haptic element optimally transform into one another at the periphery of the optic element. However, even small distances between bases are possible. Preferably, the cumulative distances between the bases of the haptic elements is less than 25%, preferably less than 15% of the circumference of the outer diameter of the haptic ring in the unloaded condition. According to a particularly preferred embodiment of the invention, the bases of the haptic elements are flush joined to the optic element, wherein an intraocular lens with two lenses is preferably at least correspondingly designed.

As alternative form designs of haptic elements, besides the dash-shaped also the T-formed haptic elements are possible, which ensure that both the equator of the intraocular lens and the optical edge of the haptic element, possibly full surfaced, transform into each other with the respective circumference of the ciliary or of the optic element, but at the same time have greater flexibility than the dash-shaped. Furthermore, the wall thickness of the haptic element can also be tapered from the base of the haptic element in order to further-increase flexibility. In addition, larger openings (pie-shaped recesses) are formed through the T-shaped haptic elements, through which the tubular reservoirs can be pulled outwards.

To be able to transmit a change in diameter of the ciliary as completely as possible in a change in diameter of the intraocular lens, in this case in particular of the optical sections and to achieve a possibly high change in refractive power, it is advantageous to form the haptic element stiffer in a further embodiment. For this purpose, the haptic element or parts of the haptic element may be formed of a material having a higher modulus of elasticity than the optic element. Alternatively, the haptic element may increase in cross section in thickness from the equator to the base of the haptic ring segment, so that it is stiffer and can flex less in the radial direction.

It was already described that the haptic element should preferably be connected flush with the optic elements so that the haptic element transforms into the optic element area without thickness steps. However, even small differences in thickness can be formed, provided that the necessary ductility of the optic element is not affected unduly. It has been found that with thickness differences of 80% to 90%, the operation is still substantially maintained.

Preferably, the optic elements of the intraocular lens are convex-concave or concave-convex and shaped as converging lenses from the anterior to posterior, that is, the lenses are thinner in the edge section than at the central optical axis. However, even one of the two lenses, preferably the posterior one can be used, also to compensate for patient-specific visual defects, and for example, adopt a bi-convex shape. In this case, larger thickness differences are tolerable.

According to a particularly preferred embodiment of the present invention, the intraocular lens has at least four, preferably at least six, and especially preferably twelve haptic elements.

The cumulative width of the constrictions, which is the narrowest portions of the T-shaped haptic elements that form in the transition of the haptic element in to the haptic ring is dependent on the modulus of elasticity of the material used and is at least 10%, preferably more than 25% of the circumference at the level of the haptic tips.

The outer diameter of the intraocular lens, particularly as ciliary intraocular lens in the production and near range is 9 mm to 13.5 mm. The diameter of the optic element of the intraocular lens in comparison is 3.5 mm to 9.5 mm, wherein the thickness at the poles is 2.5 mm to 6 mm. The wall thickness of the optic elements as a function of its modulus of elasticity is between 0.2 mm and 1.5 mm, particularly preferable between 0.5 mm and 1.2 mm. If one of the two lenses assumes a convex-convex shape, the optic element in the central optic range can be significantly thicker and assume more than 2 mm in wall thickness. The height of the cylindrical haptic ring, thus the height of the equator, where both intraocular lens half shells lie, is between 0.3 mm and 2.5 mm, preferably between 0.5 and 1.5 mm. The width or thickness of the haptic ring is between 0.5 mm and 2.5 mm.

In the case of use of the intraocular lens as a ciliary intraocular lens, the above-indicated dimensions may be somewhat smaller.

The diameter of the ciliary intraocular lens should preferably be slightly larger than the diameter of the ciliary. The ciliary intraocular lens is minimally biased. Thus, a maximum possible contraction and thus maximum possible change in diameter can be used for the accommodative power. The ciliary intraocular lens should therefore be designed preferably under this bias for the far range, that is, the intraocular lens reaches the farthest point after the deformation caused by the bias. This optical design point could also be described by a so-called "negative accommodation", while the intraocular lens is designed in a far accommodation state, beyond the farthest point. This remote point lies in the range of 5 to 200 m, preferably 50 m to 150 m. This interpretation of the intraocular lens under a bias is significant particularly in patients whose ciliary has only a very small change in diameter (for example, 0.2 mm), or contraction, and in which with the least possible change in diameter maximum refractive power change should be achieved.

The ciliary intraocular lens is designed in a flat state for far vision so that it reaches its planned design point for the far point only under a pre-deformation that is, a reduction in diameter of the haptic ring from 0.03 mm-0.5 mm, preferably 0.05 mm-0.3 mm.

The required adjustment to the size of the individual patient's eye is based on the ciliary intraocular lens only to the required diameter. In a capsular intraocular lens, there is the additional difficulty that depending on the patient, the axial width of the capsular bag can vary greatly, since the natural lens thickens with age.

Preferably, the intraocular lens is made of two half shells, which are joined by means of gluing or welding and thus connected to one another by adhesive force.

However, the intraocular lenses can also be composed of two half-shells thus be in two pieces, and be connected positively or frictionally. According to a further preferred embodiment of the intraocular lens, it is therefore intended that the tips of the haptic elements be surrounded by a thin strip or a membrane. Such a band does not limit the contractility of the haptic element. The inside of the band between haptic peaks is preferably coated as well as the side surfaces of the haptic elements with anti-proliferative substances, so that no cells can grow into the apertures.

The haptic elements are distributed preferably evenly and uniformly over the periphery of the optic element and the bases of the haptic elements lie together. The bases of the openings between the haptic elements do not extend to the optic element, whereby the depth of the openings may be smaller than the radial length of the haptic elements. According to a further embodiment of the present invention, the widths of the openings vary at the bases of the haptic elements and/or the widths of the bases of the haptic elements themselves in order to deform the optic element unevenly and thus compensate image defects, such as astigmatism of the patient. For this compensation, but also independently thereof, it is provided that the individual haptic elements of an intraocular lens have different shapes or different modulus of elasticity from the optic element. In addition, the configuration of the haptic elements of the anterior opposite the posterior intraocular lens half-shells differ with regard to their shape, width and height from each other in order to achieve an optimum elasticity and deformability adjustment with respect to the accommodation.

It was already described that with this invention, a symmetrical deformation of one or more optic elements of the intraocular lens is sought. For this purpose, the haptic elements are preferably connected in equiangular manner with the optic element. However, a symmetrical deformation of the lens or lenses can also be achieved sufficiently if a minimum number of haptic elements exist and they are not distributed exactly in equiangular manner while they have exactly the same base widths. For example, also with an intraocular lens with twelve haptic elements, the elements 3, 5 and 7 could be bisected by another slightly thinner line-shaped recess and yet a sufficiently uniform and rotationally symmetric deformation of the optic element be achieved. For 12 haptic elements, the exact strict adherence to equiangular manner of the haptic element plays a decisive role. It is important that the bases of the haptic elements be connected over almost the entire periphery of the optic element. On the other hand, for example, if only 3 haptic elements are distributed over the periphery of the optic element, they should differ only slightly from the equiangular form and identically shaped haptic elements.

The edges of the haptic elements are preferably square or sharp. However, also rounded corner edges may be provided, in particular at the inner edges of the haptic segments towards the cavity of the intraocular lens. Therefore, the haptic elements for example can be circular or elliptical in cross-section in addition to the preferred rectangular shape. The surface of the haptic elements is formed according to a preferred embodiment, structured, or provided with a biologically active coating, whereby the risk of cataract or bacterial adhesion is reduced or avoided. As coating agents, preferably polysaccharide coatings, heparin, hyaluronate or other active ingredients are provided.

To avoid stray light and glare, which happens at night in particular, the haptic elements are preferably formed diffuse, coloured, opaque, doped or surface-structured.

Furthermore, the haptic elements can be provided with a label of identification, a product code, or serial number.

The shapes of the anterior and posterior lenses or other optic elements, if necessary, can have bi-convex, planoconvex, plane-parallel, meniscus, concave-convex, or other lens shapes. The two optic elements can also have different diameters and/or different refractive indexes. When the anterior or posterior optic elements have identical refractive indices, such as the filling, the inner surfaces of the posterior or anterior optic element can be of any shape and differ from classical optic element forms.

The optic element or optic elements of the intraocular lens of this invention, particularly the outer surfaces thereof are preferably aspherical moulds, that is, they are different from the spherical shape. The radii of curvature of the optic elements increase from the central optic element axis to the edge of the optic element preferably by more than 20% and particularly preferably by more than 50%. In certain designs, the increase in radius may also be 100% or more than 300%.

According to a further preferred embodiment of the intraocular lens, it is provided that the haptic ring is connected two- or three-piece to the optic element, whereby said optic elements are frictionally held and/or positively by the haptic ring. With this, the intraocular lens is designed smaller in size and easily inserted into the eye. According to a particularly preferred embodiment, it is provided that the haptic ring is composed of a plurality of haptic ring segments, which are preferably connected by a membrane. The membranes may be arranged outside, inside or laterally of the ring. Preferably a circumferential groove and a corresponding edge for a firmer and more precise seat are provided between the haptic ring segments and the haptic element, whereby other positive connections are of course also conceivable. Alternatively, it is provided that the haptic ring consists of haptic ring segments, wherein the individual haptic ring segments are held together by a thread. This creates a kind of chain.

Furthermore, a continuous haptic ring (without individual segments) similar to the above described, could be used in principle. Preferably, the ring should be elastic and compressible in circumferential direction and in radial direction be largely not compressible. Thus, the power of the ciliary can most effectively be transmitted, especially the contraction, i.e. the change of the ciliary diameter is limited to a few tenths of a millimeter during near accommodation. Alternatively, the haptic ring for example, could also be divided in only one place.

The shown design of the intraocular lens can be used as purely optic shift intraocular lenses in which the lenses are only moved on their axis and not deformed. In addition, the intraocular lens could be implanted both in the capsular bag, or indirectly coupled to the ciliary.

Different materials come into question as suitable materials for the intraocular lens. According to an embodiment of the present invention, an intraocular lens is provided, wherein the intraocular lens consists of a silicone, in particular a thermoplastically processable silicone. Particularly polymers from the group of organopolysiloxane/polyurea/polyurethane block polymers are useful as thermoplastic silicone types. Preferably, it is provided that the silicone used is cross-linked after joining. However, also thermoplastic polymers and cross-linked thermoplastic polymers or elastomers can be used which have a high optic element transparency and, preferably, a high refractive index. Such polymers and copolymers or mixtures thereof, if necessary, may include the group of the various polyacrylates and polymethacrylates (as well as "PHEMA", "PHPMA", etc.), poly-n-butyl methacrylate) (PBMA), polyvinyl (polystyrene, polyvinyl acetate, poly-N-vinylpyrrolidones "PNVP"), ethylene vinyl acetates, the group of polysiloxanes (PDMS), polyphosphazenes, polyurethanes, polyureaurethanes and their copolymers including $NH_2$- or OH-terminated polyisobutylene polyurethanes, other hydrogels including polyethylene glycol-based hydrogels, polysulfones; styrene-ethylene-butylene-styrene-based thermoplastic elastomers (SEBS), or hydrogenated styrene block copolymers, polystyrene-block-isobutylene-block-styrene (SIBS), include polypropylene. Among these polymers, preferably polystyrene-block-isobutylene-block-styrene (SIBS) or polyurethanes based on $NH_2$- or OH-terminated polyisobutylene are used. The implant material must also be biocompatible and bio-stable. The polymers are thus surface-modified to improve their biocompatibility, which is preferably carried out by hydrophilisation. The polymers may also be water permeable.

The filling in particular can be made of a super-elastic polymer or liquid. In addition to the aforementioned polymers, in particular other hydrophilic polymers are suitable, such as polyvinylpyrrolidone, polyvinyl alcohol, or hyaluronic acid. These can be mixed with water, particularly suitable for this purpose is also linked polyvinylpolypyrrolidone (PVPP). The liquid can be water or an aqueous dispersion or colloiddispersed solution in which nano-particles preferably made of polymers are added to increase the refractive index. In particular, the filling may also be made of halogen-ated hydrocarbons, in which polymethyl methacrylate particles are added. The nano-particles may also have functionally adapted surface or be coated with noble metal colloids (for example, gold). Furthermore, gold sole is useful as a filling liquid.

To increase the refractive index of the polymers or of the filling medium, other nano-particles, such as titanium dioxide may be added. Preferably, the polymer nano gold can be added or bonded to it chemically (covalently). If gold is added, the intraocular lens obtains anti-bacterial properties. In addition, the polymer or the filling can thus filter blue light, which protects the retina as a UV barrier.

The modulus of elasticity of the polymer according to an advantageous embodiment is less than 1 $N/mm^2$. The modulus of elasticity of the shell or half shells of the ciliary intraocular lens is further preferably less than 0.5 $N/mm^2$, and preferably greater than 0.02 $N/mm^2$. It should be noted that, in particular in the area of haptic arms at which the half-shells are joined together, the modulus of elasticity values compared to those listed above might be higher. The modulus of elasticity of the filling is preferably less than 0.05 $N/mm^2$ and more preferably less than 0.01 $N/mm^2$. In one embodiment of the intraocular lens as capsular intraocular lens, the modulus of elasticity of the shell can be higher than the above-indicated values for the shell.

The intraocular lens according to the present invention can be used also for other technical purposes, for example as a continuously focusable optic element for 3D endoscopes equipped with an integrated camera, PC monitors for high-quality video conferencing or autofocus lenses in the low-cost sector. The accommodation here could be controlled over radially acting actuators, such as with an air-filled or fluid-filled hose.

It has already been indicated that the present invention relates to a process for the implantation of an intraocular lens having an optic element, a haptic element, and a filling. According to the invention, it is provided for this purpose that the intraocular lens is folded or rolled for reducing the volume so that the filling is at least partially disposed in the reservoir and the filling is at least partially pressed from the reservoir into the cavity after implantation. Preferably, the expandable portion of the reservoir is disposed outside the intraocular lens during implantation. The inventive method is especially suitable for intraocular lenses, as described in the remainder of the present application.

Finally, an intraocular lens with a liquid or gel filling is to be created, which is implanted in a smaller state. According to the invention it is therefore provided that one or more reservoirs with the filling are preferably detachably connected via a tube to the cavity, so that, for a change in volume of the cavity during accommodation or folding of the intraocular lens for implantation the filling can be transferred into the reservoir and vice versa.

As the following figures show, the volume of the intraocular lens for the implantation process is substantially reduced by the method. This is made possible in particular by the construction of the intraocular lens consisting of a relatively thin shell and a large filling. In the calculation of volume change of the lens, if one bases the volume on the part of the intraocular lens without the haptic element, that is, on the diameter at the equator of the optic element and/or of the cavity, then the volume can be reduced by more than 20%, preferably by more than 30% and most preferably by more than 40% if the lens flattens and the filling presses in the reservoir/s. An advantage of this arrangement and procedure is that in normal operation, i.e. after implantation, you may dispose the reservoirs preferably with a very small diameter posterior on the haptic ring and along the haptic ring. The reservoirs do not disturb the optical section of the intraocular lens. For the implantation process, the diameter of the tube can swell by absorption of the filling by up to 8 times its diameter.

If for instance the reservoir were integrated in haptic ring, thus the haptic ring the reservoir itself, then the haptic ring "for the swelling" should be designed relatively elastic and soft, but then the haptic ring would also be easily compressible or too soft in the radial direction, so that the haptic ring could transmit the forces of the ciliary inadequately and hence enormous losses would occur for the deformation of the intraocular lens during accommodation.

Another special feature in the design of the reservoir is obtained when the reservoir serves as volume compensation during accommodation. Typically, the volume of the filling in near range is then somewhat greater than in the far range of the intraocular lens. The volume amount of filling is now preferably equal to or less than the smaller volume, usually rated for the far range. In order for the volume of filling to increase in the intraocular lens for the near range during accommodation, the tube moves into a flat shape, for example from a circular cross section into an ellipse shape, together, thus reducing its volume. A kind of suction effect occurs from the lens to the reservoir. Because the reservoir and the tube collapse from its normal/production state and contracts, the otherwise necessary initial resistance to be overcome to expand the tube is avoided. This initial resistance cannot be overcome by the accommodation process, even if the tube has very thin walls. The initial resistance to swell the reservoir, however, can be overcome if the intraocular lens for the implantation process is pressed flat and subsequently rolled up. It should be noted further that the preferred design of the quantity of filling for the smaller volume condition or far range is also true for an intraocular lens whose production state is in the near range and consequently the reservoir during filling must be compressed somewhat in order to exclude air in the reservoir.

Specific embodiments of the present invention are explained as follows and with reference to the Figures. Shown in the drawings:

FIG. 1a, b: depending on a schematic representation of an implanted ciliary intraocular lens, FIGS. 2a-3i: Intraocular lenses in different perspectives, FIG. 4: an intraocular lens with various recesses, FIG. 5a, b: Exploded views of different intraocular lenses and FIG. 6a-l: various intraocular lenses with reservoirs.

FIGS. 1a and b each show a sectional view of an eye 1 with the cornea 2 and the sclera 3 and a ciliary intraocular lens 4. The intraocular lens 4, in direct contact with the ciliary muscle 5, so that the force of contraction is transmitted directly to the ciliary intraocular lens 4. In order to achieve a uniform deformation of the optic element 6, 7 a possibly large contact surface 9 for the ciliary muscle 5 is formed, which extends along the haptic ring 10. In order to be able to contract the haptic ring 10 sufficiently, the haptic ring 10 in the embodiment shown is divided into haptic ring segments 11, which are spaced slightly from one another in the unloaded state. Furthermore, the haptic elements at the transition to the optic 6, 7 are linked with one another. Further details also on different types of intraocular lenses 4 are described below with reference to the figures. It should be noted that also the capsular bag, or parts thereof, and/or the zonular fibres could lie between ciliary and contact surface of the intraocular lens.

FIGS. 2a-e show a concrete embodiment of an intraocular lens in 4 different perspectives. In the perspective view (FIG.

2a) it can be clearly seen that the anterior and posterior optic element 6, 7 and—in the embodiment shown—12 haptic elements 8 are connected to each other. The haptic elements 8 are spaced apart by radially guided line-shaped recesses 12, so that, both at the contact surface 9 and at the transition between the haptic elements 8 and the optic element 6, 7 greatest possible surface is created for power transmission To avoid slipping of the intraocular lens 4 within the ciliary 5, the contact area in the cross-section is formed V-shaped (arrow 13).

Figure 2D:
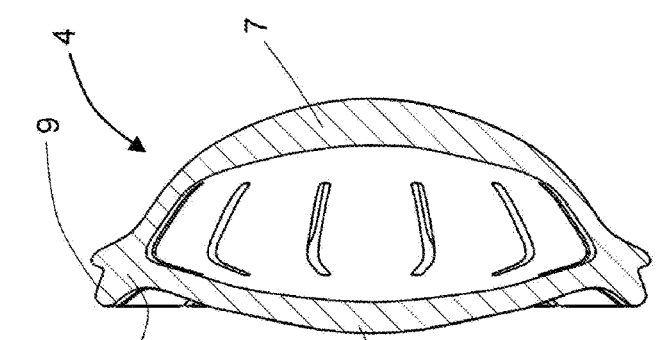
Figure 2E:
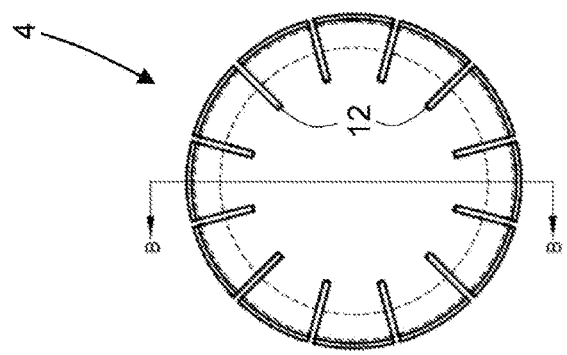

The differently shaped intraocular lenses 4 during the accommodation are shown schematically in FIGS. 2c and d. In the flat and non-deformed state (FIG. 2c), the intraocular lens 4 serves near vision. For far vision, however, the contracted ciliary 5 and the lenses 6, 7 are deformed towards larger curvatures (FIG. 2d).

Among the embodiments illustrated in FIGS. 1a to 3g, the recesses 12 are formed line-shaped. Such recesses 12 are relatively easy to introduce into the intraocular lenses, wherein three different ways are essentially intended, up to where the recesses 12 are introduced or cut. FIG. 3b shows a variant in which the recess 12 is guided up to the edge of the optic area of the intraocular lens 4, whereby the cavity 15 between the optic element 6, 7 (arrow 14) is opened. On the other hand, the recess 12 in the embodiment of FIG. 3c also extends to the edge of the optical system 6, 7, wherein a thin membrane 16 is not broken, and the cavity 15 is thus not open. Finally, FIG. 3d shows an embodiment in which the recesses 12 end within the haptic element 8, whereby the cavity 15 also remains closed.

The intraocular lens 4 can be formed integrally or consist of two half-shells 18a, 18b, which are connected with the haptic element 8, positively, non-positively or materially bonded (FIGS. 3f to 3g).

FIG. 3g shows in particular a possible division of the two intraocular lens half-shells 18a, 18b, which facilitates a concentric assembly of the two half-shells 18a, 18b and enables a form-fit connection (arrow 17) in that the connecting surfaces have corresponding steps 19. Through different step heights in individual haptic elements, an angular aligning of two half shells 18a, 18b is possible. An angular aligning of the half-shells 18a, 18b is particularly advantageous for intraocular lenses 4, in which the half-shells 18a, 18b have different modulus of elasticity. The sectional view of FIG. 3g, moreover, shows that the optic elements, haptic elements, and also the filling may be composed of different materials with different elastic modulus.

Figure 3I:
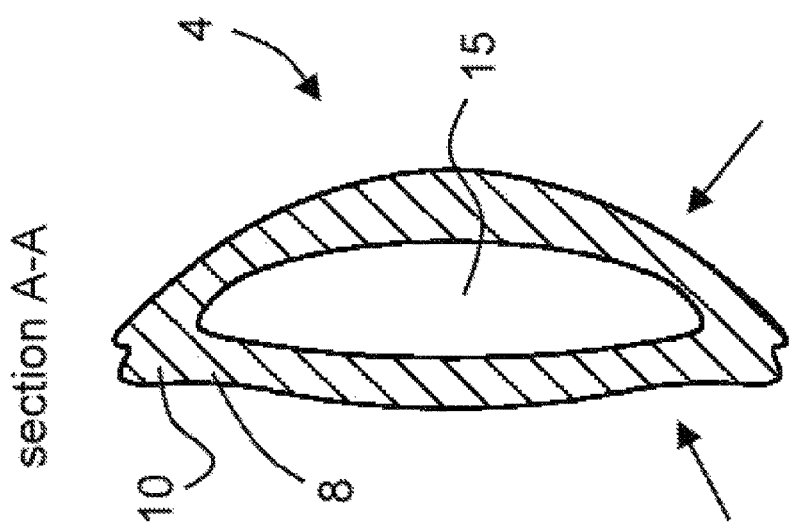
Figure 3H:
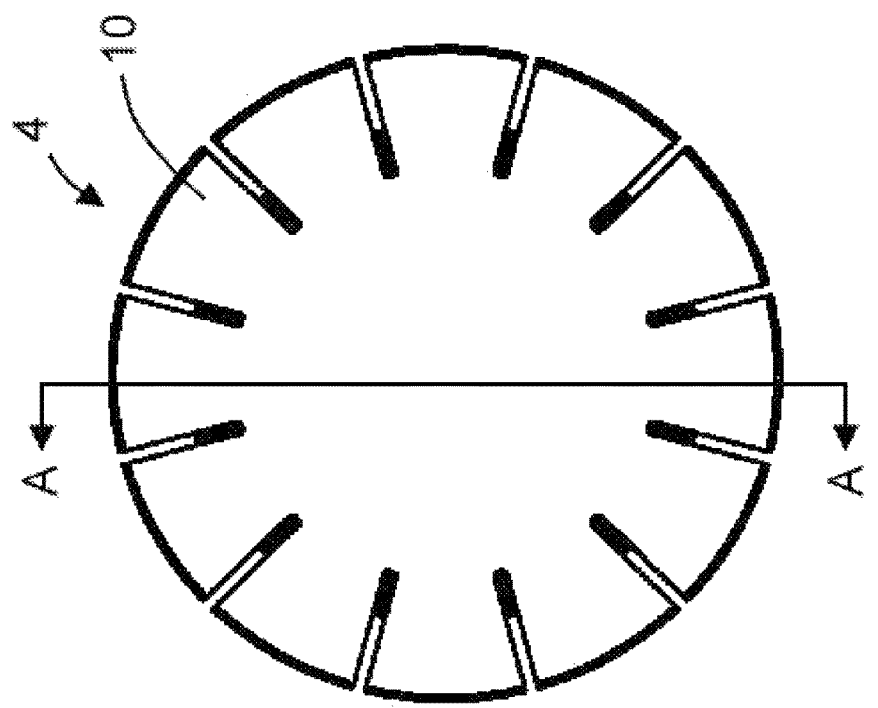

FIGS. 3h and 3i show an embodiment of an intraocular lens 4 with a haptic ring 10, which is designed wider in cross-section and thus with respect to the previous embodiments is stiffer, so that the haptic ring 10 may deform less in the radial direction and hence effectively transmits the change in diameter of the ciliary to the optic element. Here, the smallest wall thicknesses of the half shells do no longer lie in haptic ring 10 or at the equator of the cavity 15 as in the previous versions, but shift to the base of the haptic element 8 and/or to the optic edge (see arrows in FIG. 3i).

Figure 4:
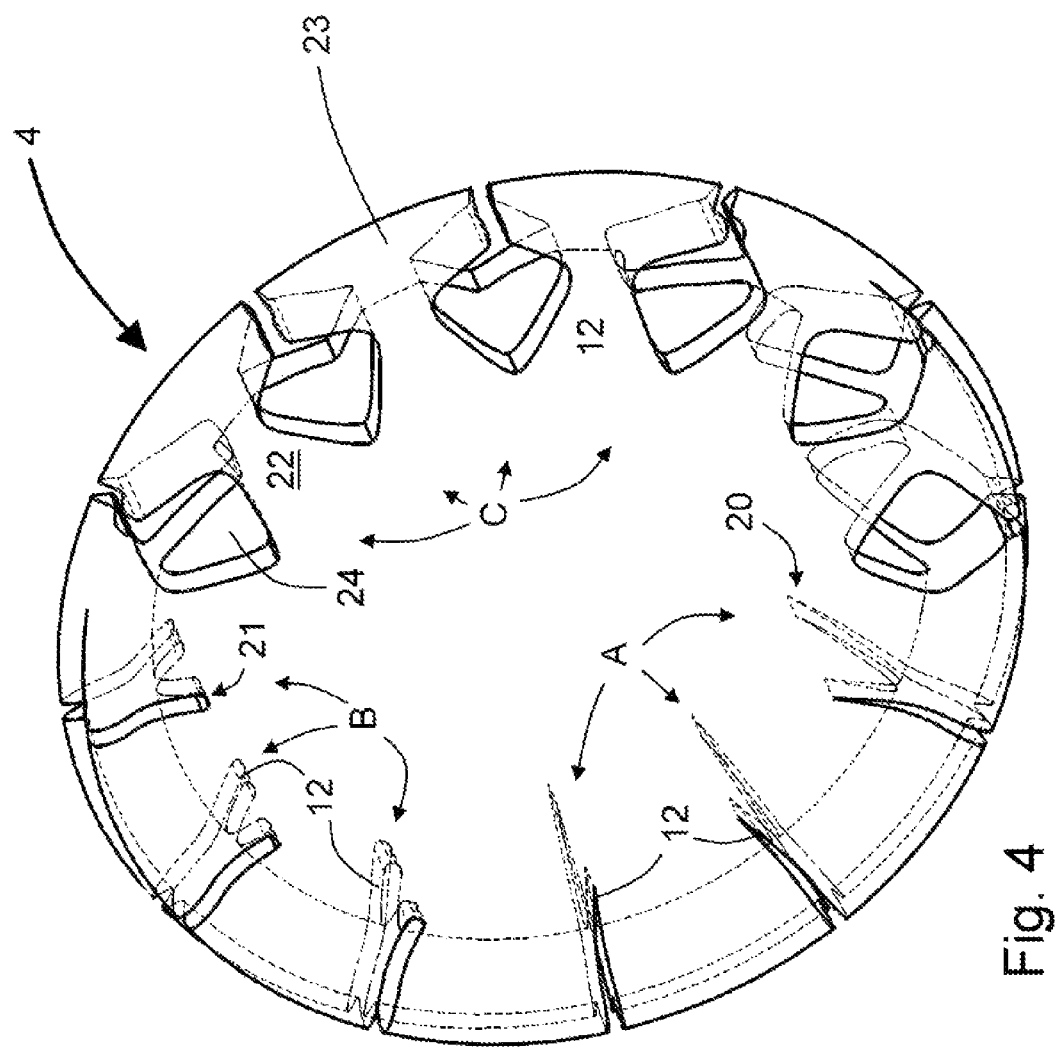

As can be derived from the schematic representation of FIG. 4, different forms of recesses 12 are provided. The variants A and B show line-shaped recesses 12, where the side surfaces of the recesses 12 in variant A converge at an acute angle (arrow 20), whereas in variant B, a rounded transition is provided (arrow 21). A particularly preferred geometry is shown in variant C. according to which the haptic element 8 consist of substantially trapezoidal portions that converge on the side opposite the optic element 6, 7 at an acute angle (reference number 22). There, the haptic elements 8 form the part-annular haptic ring segment 23, wherein adjacent haptic ring segments 23 are spaced slightly from one another in the shown unloaded state. This creates a pie-shaped recess (12) between two haptic elements 8. The haptic elements with the recesses of variant C are thus similar to the T-shaped haptic elements. The haptic elements with the line-shaped recesses form figuratively trapezoidal sections with obtuse diverging sides to which the part-annular haptic ring segments seamlessly connect, thus in overall forming a trapezoidal or line-shaped haptic element.

In the illustrated embodiments, the cavity 15 is opened by the recesses 12, so that the openings 24 are formed. These openings 24 can be closed by means of a thin membrane, without the elasticity of the intraocular lens 4 being influenced.

Figure 5B:
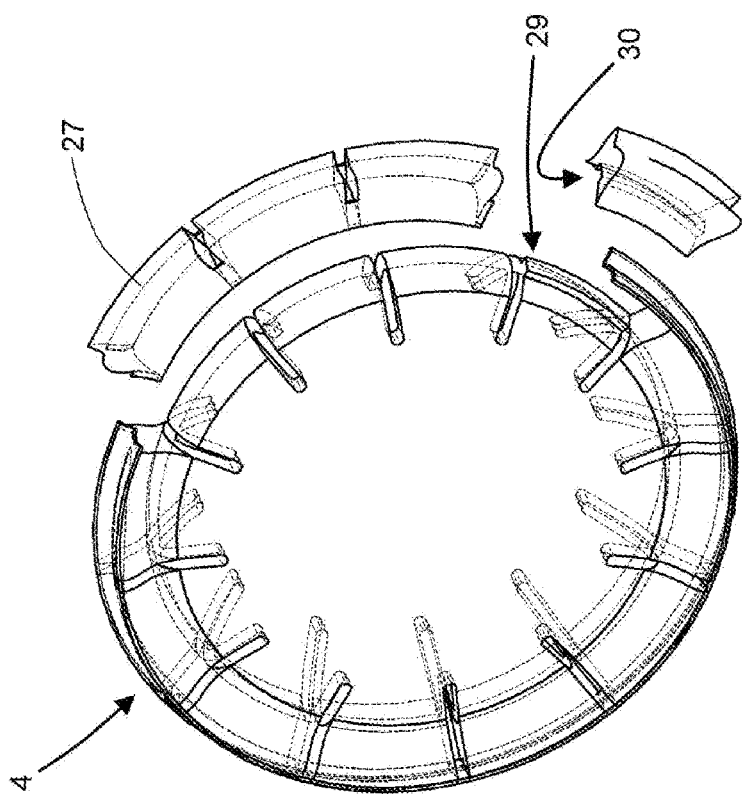
Figure 5A:
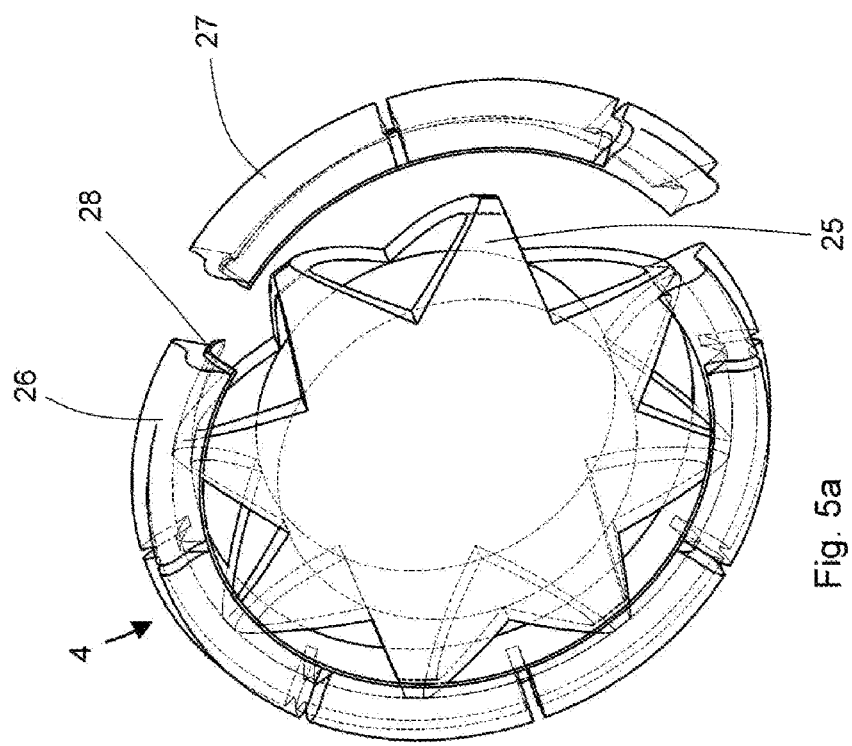

According to another specific embodiment of the present invention, it is provided that the intraocular lenses are designed divided by 4 to make them easier to introduce into the eye. FIGS. 5a, b show embodiments in which the ciliary intraocular lens 4 consists of a comparatively small intraocular lens 25 and a separate haptic ring 26. The separate haptic ring 26 is divided by openings or 24 in a plurality of segments 27 that are connected to each other with 28 membranes. FIG. 5a shows an embodiment wherein the membrane 28 is disposed inside, wherein, in the variant according to FIG. 5b, the membrane 28 is disposed outside or laterally, as shown in the pulled-out three-segment of the exploded view. Furthermore, at the contact surface between the separate haptic ring 26 and the intraocular lens 25 groove- or tongue-shaped contours 29, 30 may be provided in order to provide a stable grip. The internal intraocular lens 25 may also be designed differently, whereby the described embodiments are preferred.

According to a concrete embodiment of the present invention, the cavity 15 formed between the half shells 18a, 18b, has a filling 32 that rests within a bag or, if necessary, a cavity demarcated by membrane 31. In the accommodation, not only the optic elements 6, 7 are deformed, but also the surface of the bag or the membrane 31 and the filling 32, which has different effect on the refractive power. According to a concrete embodiment of the invention, reservoirs 33 are provided, which are connected hydraulically to the cavity 15, detachably or permanently to be able to implant such an intraocular lens 4 with a filling 32 inside the eye, and allow change in volume of the cavity 15 during accommodation.

Figure 6L:
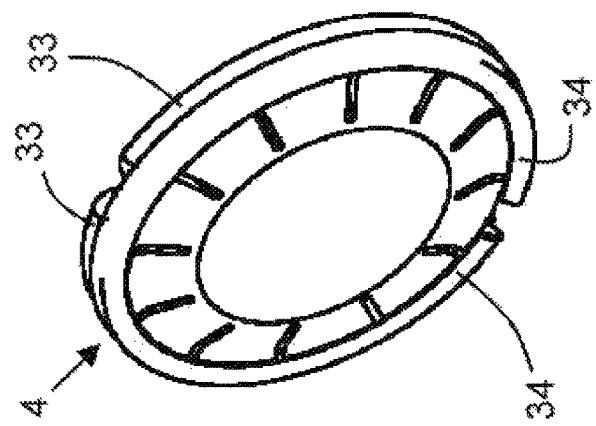

In FIGS. 6a to 6l, various embodiments of such intraocular lenses 4 having with a filling 32 and at least one reservoir 33 are shown. In the embodiment of FIGS. 6a to 6e, a single reservoir 33 is provided which is disposed outside the tube-shaped intraocular lens 4. FIGS. 6a, b show the situation in which the filling 32 is almost completely disposed within the cavity 15. In contrast, FIGS. 6c, d shown how the filling 32 is located within the reservoir 33 and also the intraocular lens 4 is relatively flat. Due to simpler fabrication, the tubular reservoir 33 as shown in FIG. 6a preferably has a uniform diameter. Here, however, the portion of the tube close to the intraocular lens has a greater wall thickness than the rest of the tube, so that only the part of the tube with the smaller wall thickness for receiving the filling inflates (FIG. 6c, d). In a short transition section, different wall thickness equalise. Of course, the tubular reservoir can also have different diameters along its length.

Prior to implantation, the filling 32 can be pressed in the required amount from the cavity 15 into the reservoir 33, so that the intraocular lens 4 can be rolled up or folded (FIG.

6e). The reservoir 33 extends further outside of the intraocular lens 4, so that the implantation can be carried out through a minimum section.

As an alternative to the embodiment in which the reservoir 33 extends outside of the intraocular lens 4, the reservoir 33 may also be disposed within the intraocular lens 4 (FIGS. 6f to 6i). For this purpose, it is tube-shaped and placed between the haptic elements 8, so that the optical characteristics thereby are not affected.

Figure 6K:
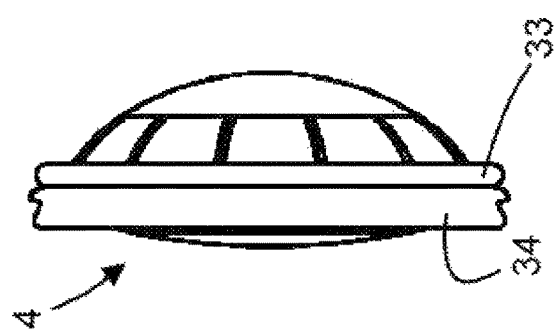
Figure 6I:
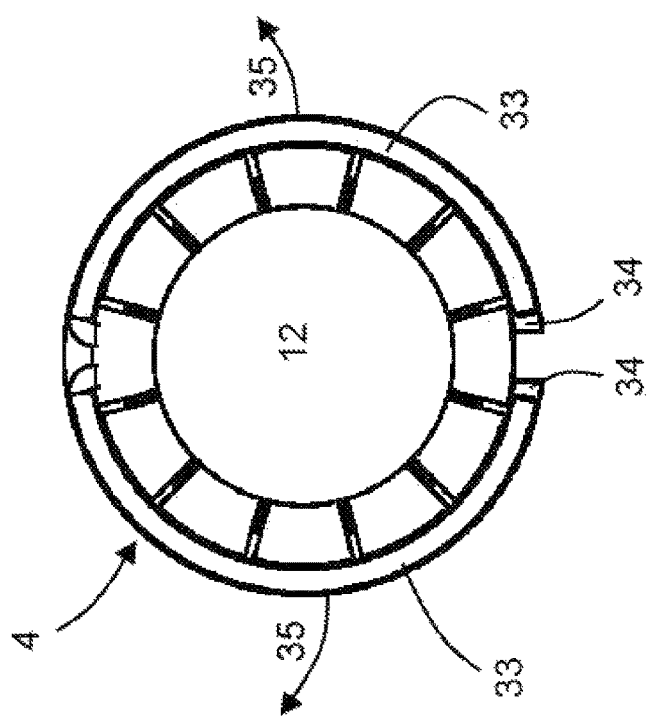

Finally, embodiments are also provided in which two or more reservoirs 33 receive the filling 32. FIGS. 6j to 6l show a configuration with two reservoirs 33 that surround the intraocular lens 4 by 180°. In addition, the intraocular lenses 4 have another ring or two ring elements 34 that also surround the intraocular lens 4 in each case by 180°. The ring members 34 are connected to the reservoirs 33 and a haptic element 8, and can be pivoted together with the reservoirs 33 in the direction of arrow 35 in order to have a compact design of the intraocular lens 4 for implantation. The ring members 34 can slide over the haptic elements 8 and thus compensate the change in diameter related to the ciliary.

EXPLANATION

The work that led to this invention was funded in accordance with the grant agreement No. CP-1P 214491-2 COTECH under the Seventh Framework Programme of the European Union ([FP7/2007-2013] [FP7/2007-2011]).

The invention claimed is:

1. A ciliary intraocular lens, with at least one optic and one haptic, wherein
   the haptic is composed of a plurality of haptic elements, which are preferably connected with the optic in equiangular manner, wherein
   a) the haptic elements have an essentially trapezoidal portion in a plan view and the bases of two adjacent haptic elements are connected to each other at the transition to the optic and
   b) the haptic elements on the side of the trapezoidal portions facing away from the optic have a part of annular haptic ring segment, wherein the haptic ring segments of two adjacent haptic elements in the unloaded state are spaced slightly away from one another, so that an essentially cake-piece or line-shaped recess is formed between two adjacent haptic elements.

2. The intraocular lens according to claim 1, wherein the intraocular lens at least has an anterior and a posterior optic, which are connected to each other via the haptic, wherein a cavity is formed by the anterior and posterior optic as well as the haptic and at least the optic area of the cavity has a filling.

3. The intraocular lens according to claim 2 wherein the area of the cavity, which is bounded by the haptic and/or the recesses is occupied partially or completely by the filling.

4. The intraocular lens according to claim 2 wherein the filling is liquid, gel-like, or gaseous and preferably comprises nano-particles.

5. The intraocular lens according to claim 2 wherein the filling has a higher refractive index than the aqueous humour.

6. The intraocular lens according to claim 2, wherein one or more reservoirs with the filling are preferably detachably connected via a tube to the cavity, so that, for a change in volume of the cavity during accommodation or folding of the intraocular lens for implantation the filling can be transferred into the reservoir and vice versa.

7. The intraocular lens according to claim 6 wherein the reservoir is tubular and is preferably connected with the cavity via a micro-valve or a hollow needle or cannula.

8. The intraocular lens according to claim 6 wherein the reservoir is connected with the cavity via a tube, which is separable by melting.

9. The intraocular lens according to claim 6, wherein the connection point between the reservoir and the cavity is disposed on the membrane, on the haptic or outside the optic area of the optic.

10. The intraocular lens according to claim 2, wherein the filling is at least partially enclosed within the cavity by a membrane, wherein the membrane is preferably permeable to water.

11. The intraocular lens according to claim 1 wherein the haptic and/or haptic ring segments have respectively an anterior and a posterior piece that are connected to each other at the equator.

12. The intraocular lens according to claim 1 wherein the anterior optic or the posterior optic at the edge area are formed thin or thinner than at the central optical axis.

13. The intraocular lens according to claim 1 wherein the recesses are closed with a membrane or a skin.

14. The intraocular lens according to claim 1 wherein the recesses are aligned radially from the equator of the haptic and
   a) terminate within the haptic,
   b) lead up to the equator of the optics or
   c) extend beyond the equator of the optics.

15. The intraocular lens according to claim 1 wherein in the unloaded state the cumulative width of the recesses on the outer diameter of the haptic ring is less than 25%, preferably 2-15%, of the circumference.

16. The intraocular lens according to claim 1 wherein the cumulative spaces of the bases of the haptic elements is less than 25%, preferably less than 15%, of the circumference of the outside diameter of the haptic ring.

17. The intraocular lens according to claim 1 wherein for maximum force transmission the haptic ring in the maximum loaded state is fully circumferential in contact with the ciliary.

18. The intraocular lens according to claim 1 wherein the bases of the haptic segments are connected flush with at least one of the optics.

19. The intraocular lens according to claim 1 wherein the haptic ring segment form a cylindrical outer contour, wherein the haptic ring segment in cross-section are configured preferably in V-shape.

20. A ciliary intraocular lens, with at least one optic and one haptic, wherein:
   the haptic is composed of a plurality of haptic elements connected with the optic in equiangular manner, wherein
   a) the haptic elements have a generally trapezoidal portion in a plan view and the bases of two adjacent haptic elements are connected to each other at the transition to the optic and
   b) the haptic elements on the side of the trapezoidal portions facing away from the optic have a part of annular haptic ring segment, wherein the haptic ring segments of two adjacent haptic elements in the unloaded state are spaced slightly away from one another and the cumulative width of the recesses on the outer diameter of the haptic ring is less than 25% of the circumference, so that a generally cake-piece or line-shaped recess is formed between two adjacent haptic elements.

\* \* \* \* \*